United States Patent [19]
Morimoto et al.

[11] Patent Number: 4,833,236
[45] Date of Patent: May 23, 1989

[54] ERYTHROMYCIN DERIVATIVES

[75] Inventors: Shigeo Morimoto, Saitama; Yoko Takahashi, Ageo; Yoshiaki Watanabe, Kodaira; Takashi Adachi, Kuki; Toshifumi Asaka, Ageo; Kaoru Sota, Tokorozawa, all of Japan

[73] Assignee: Taisho Pharmaceutical Co., Ltd., Japan

[21] Appl. No.: 43,470

[22] Filed: Apr. 28, 1987

[30] Foreign Application Priority Data

May 2, 1986 [JP] Japan ............................. 61-102882

[51] Int. Cl.$^4$ ...................... C07H 17/08; A61K 31/71
[52] U.S. Cl. ........................................................ 536/7.2
[58] Field of Search ............................ 536/7.2; 514/29

[56] References Cited

U.S. PATENT DOCUMENTS

| | | | |
|---|---|---|---|
| 4,331,803 | 5/1982 | Watanabe et al. | 536/7.2 |
| 4,382,085 | 5/1983 | Sciavolino et al. | 514/29 |
| 4,670,549 | 6/1987 | Morimoto et al. | 536/7.2 |
| 4,672,056 | 6/1987 | Fernandes et al. | 514/29 |
| 4,672,109 | 6/1987 | Watanabe et al. | 536/7.2 |
| 4,680,386 | 7/1987 | Morimoto et al. | 536/7.4 |
| 4,681,872 | 7/1987 | Freiberg et al. | 514/29 |
| 4,740,502 | 4/1988 | Hannick et al. | 514/29 |
| 4,743,593 | 5/1988 | Hunt | 514/29 |

FOREIGN PATENT DOCUMENTS

| | | | |
|---|---|---|---|
| 0184921 | 6/1986 | European Pat. Off. | 514/29 |
| 58-49396 | 3/1983 | Japan. | |
| 61-200998 | 9/1986 | Japan | 536/7.2 |

OTHER PUBLICATIONS

Morimoto et al.; J. Antibiotics 37(2): 187–9, Feb. 1984.

Primary Examiner—Ronald W. Griffin
Assistant Examiner—Nancy S. Carson
Attorney, Agent, or Firm—Lorusso & Loud

[57] ABSTRACT

Erythromycin derivatives represented by the general formula

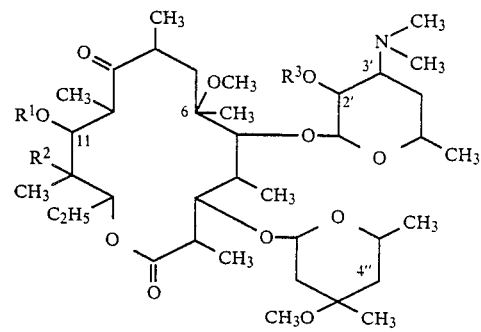

wherein $R^1$ is a hydrogen atom or a methyl group, $R^2$ is a hydrogen atom or a hydroxy group, $R^3$ is a hydrogen atom, a lower alkanoyl group, an alkoxycarbonyl group or an alkylsuccinyl group, and the salts thereof are disclosed. These compounds have antibacterial activity.

5 Claims, No Drawings

ERYTHROMYCIN DERIVATIVES

BACKGROUND OF THE INVENTION

1. Field of the Invention

The present invention relates to antibiotics 4"-deoxy-6-O-methyl-erythromycins and the salts thereof which are useful as antibacterial agents.

2. DESCRIPTION OF THE PRIOR ART

Many erythromycin derivatives have been prepared to improve their biological and pharmacological properties. For example, it is reported that 6-O-methyl and 6,11-di-O-methyl derivatives of erythromycins are more stable under acidic conditions and have stronger antibacterial activity especially, in vivo antibacterial activity than erythromycins when administered orally (U.S. Pat. No. 4,331,803 and European Pat. No. 80,818). Furthermore, 4"-deoxyerythromycin A and B are reported in Japanese Patent Application Laid-Open No. 49396/83.

SUMMARY OF THE INVENTION

An object of the present invention is to provide novel erythromycin derivatives which have strong antibacterial activity and are useful as medicines.

DETAILED DESCRIPTION OF THE INVENTION

The compounds of the present invention are 4"-deoxyerythromycin derivatives represented by the general formula

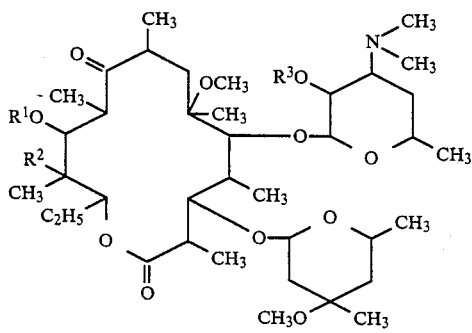

wherein $R^1$ is a hydrogen atom or a methyl group, $R^2$ is a hydrogen atom or a hydroxy group, and $R^3$ is a hydrogen atom, a lower alkanoyl group, an alkoxycarbonyl group or an alkylsuccinyl group, and the salts thereof.

The compounds of the present invention are structurally characterized by having a methoxy group at the 6-position of the macloride ring and by having no oxy group at the 4"-position of the cladinose ring. Furthermore, the compounds of the present invention are novel compounds which have strong in vitro and in vivo antibacterial activity against Gram-positive bacteria including erythromycin resistant bacteria and Gram-negative bacteria when compared with the prior art compounds, for example, erythromycin A, 4"-deoxyerythromycin A and 6-O-methylerythromycin A.

In the present invention, the term "lower alkanoyl group" means those having 2 to 4 carbon atoms such as, for example, an acetyl group, a propionyl group, a butyryl group, an isobutyryl group and the like, and the term "alkoxycarbonyl group" means a methoxycarbonyl group, an ethoxycarbonyl group, an alkoxycarbonyl group which is substituted with a phenyl group (e.g., a benzyloxycarbonyl group) or with a lower alkenyl group (e.g., an allyloxycarbonyl group). The term "alkylsuccinyl group" means a lower alkylsuccinyl group such as a methylsuccinyl group, ethylsuccinyl group, propylsuccinyl group, butylsuccinyl group and the like.

The term "salt" means pharmaceutically acceptable salts with organic acids such as acetic acid, propionic acid, butyric acid, formic acid, trifluoroacetic acid, maleic acid, tartaric acid, citric acid, stearic acid, succinic acid, ethylsuccinic acid, methanesulfonic acid, benzenesulfonic acid, p-toluenesulfonic acid, laurylsulfonic acid, malic acid, aspartic acid, glutamic acid and the like; inorganic acids such as hydrochloric acid, sulfuric acid, phosphoric acid, sulfonic acid, hydroiodic acid and the like; and carboxyvinylpolymers such as high polymer of acrylic acid.

Preferred compounds of the present invention are those of formula I wherein $R^1$ is a hydrogen atom and $R^3$ is a hydrogen atom, an acetyl group, a propionyl group or ethylsuccinyl group.

The compound of formula I wherein $R^3$ is a hydrogen atom can be prepared, for example, by the following method.

2'-O,3'-N-bis(benzyloxycarbonyl)-N-demethylerythromycin A (or B) is reacted with 1,1'-thiocarbonyldiimidazole in a suitable solvent (e.g., 1,2-dichloroethane, dichloromethane, benzene, toluene and the like) at 0° to 80° C. to give a 4"-(1-imidazolyl)thiocarbonyl derivative.

Subsequently, the 4"-(1-imidazolyl)thiocarbonyl derivative is reacted with 1 to 10 equivalents of methyl iodide in a reaction solvent in the presence of 1.0 to 2.0 equivalents of a suitable base (e.g., potassium hydroxide, sodium hydroxide, potassium hydride, sodium hydride, potassium tert-butoxide and the like) in order to methylate the hydroxy group at the 6-position. Dimethyl sulfate, methyl p-toluenesulfonate, methyl methanesulfonate and the like can be used in place of methyl iodide. Examples of the reaction solvent used are polar aprotic solvent such as N,N-dimethylformamide, dimethyl sulfoxide (DMSO), and a mixture of these solvents and a solvent such as tetrahydrofuran, 1,2-dimethoxyethane (DME), dioxane, ethyl acetate and the like. The reaction can be carried out at 0° C. to room temperature.

Subsequently, elimination of 4"-(1-imidazolyl)-thiocarbonyloxyl group of the 6-O-methyl derivative obtained above gives a 4"-deoxy derivative (elimination of the 4"-oxy group). This elimination can be followed by the reaction of the 6-O-methyl derivative with an excess amount (2-8equivalents) of tributyltin hydride and a catalytic amount of α,α'-azobis(isobutyronitrile) in an inert-reaction solvent such as benzene, toluene and the like. The reaction temperature is usually below the boiling point of the solvent used. Since the progress of the reaction can be followed by thin layer chromatography over silica gel, the reaction is turned off after the disappearance of the 4"-(1-imidazolyl)thiocarbonyl derivative, but usually the reaction is completed in 4–5 hours.

Next, the 4"-deoxy derivative obtained above is reacted with ammonium formate in methanol in the presence of palladium-carbon catalyst in order to eliminate the benzyloxycarbonyl groups at the 2'-O- and 3'-N-positions by reduction so that 4"-deoxy-6-O-methyl-3"-N-monomethyl-erythromycin A (or B) may be obtained (reductive elimination of the protecting groups). Triethylamine formate, sodium formate, formic acid and a mixture thereof may be used in place of ammonium formate. Ethanol, N,N-dimethylformamide and the like may be used in place of methanol. The reaction can be carried out usually at room temperature to the boiling point of the solvent used.

Although the 3'-N-monomethyl derivative thus obtained is isolated according to the ordinary work-up procedure, an aqueous formaldehyde and formic acid are added to the reaction solution without any isolation of the derivative, and the mixture is stirred at 40° C. to the temperature of the boiling point of the solvent for 2 to 5 hours to give a 3'-N-dimethyl derivative in good yield, namely 4''-deoxy-6-O-methylerythromycin A (or B) which is the compound of formula I wherein $R^3$ is a hydrogen atom (reductive N-methylation).

The reductive elimination of the protecting groups and reductive N-methylation described above can be efficiently carried out by the ordinary catalytic reduction. Namely, the 4''-deoxy derivative can be reacted in an alcoholic solvent (e.g., ethanol, methanol and the like) in the presence of palladium-black or palladium-carbon catalyst under a hydrogen atmosphere with stirring. The addition of formic acid, acetic acid and the like is convenient for the progress of the reaction. After the elimination of the benzyloxycarbonyl group, the hydrogenation proceeds effectively by the addition of formaldehyde (usually 2 to 8 equivalents) to the reaction solution so that the N-methylation is efficiently carried out.

In the methylation of the hydroxy group at the 6-position, the use of large amounts of the base and methyl iodide promotes the methylation of the hydroxy groups at the 11-position as well as the 6-position. The resulting 6,11-di-O-methyl derivative is subjected to, in turn the above-mentioned elimination of the 4''-oxy group, reductive elimination of the protecting group and reductive N-methylation to give the corresponding 4''-deoxy-6,11-di-O-methylerythromycin A (or B) which is the compound of formula I wherein $R^3$ is a hydrogen atom.

Alternatively, the methylation of the hydroxy group at the 6-position can be carried out prior to the introduction of the 4''-(1-imidazolyl)thiocarbonyl group.

Furthermore, the compound of formula I wherein $R^3$ is other than a hydrogen atom can be obtained by the introduction of the 4''-(1-imidazolyl)thiocarbonyl group, the 6-O-methylation and the elimination of the 4''-oxy group as described above using an erythromycin A (or B) having $R^3$ other than a hydrogen atom at the 2'-O-position in place of 2'-O,3'-N-bis(benzyloxycarbonyl)-N-demethyl-erythromycin A (or B) as a starting material. This starting material can be obtained by the reaction of erythromycin A (or B) with an acylating agent having $R^3$ other than a hydrogen atom. Examples of the acylating agent are acid anhydrides (e.g., acetic anhydride, propionic anhydride, butyric anhydride, succinic anhydride, malonic anhydride and the like), acid halides (e.g., acetyl chloride, acetyl bromide, propionyl bromide, methylsuccinyl chloride, ethylsuccinyl chloride, ethylmalonyl chloride and the like) and chloroformate (e.g., ethoxycarbonyl chloride, allyloxycarbonyl chloride, benzyloxycarbonyl chloride and the like).

The compound of formula I wherein $R^3$ is other than a hydrogen is subjected to solvolysis at the 2'-O-position to give the compound of formula I wherein $R^3$ is a hydrogen atom. This solvolysis is carried out in a mixture of an aqueous sodium bicarbonate solution and methanol with stirring.

The compound of formula I wherein $R^3$ is other than a hydrogen atom can be also obtained by the 2'O-acylation, the introduction of the 4''-(1-imidazolyl)thiocarbonyl group and the elimination of the 4''-oxy group as described above using 6-O-methylerythromycin A (or B) or 6,11-di-O-methylerythromycin A (or B) as a starting material. These compounds can be obtained by the above acylation of the 4''-deoxo derivative.

Since the progress of the reactions in the above-mentioned procedures can be followed by thin layer chromatography over silica gel, high-performance liquid chromatography and the like, the reactions can be turned off after the disappearance of the starting material.

The compounds obtained in the reaction stages can be isolated from the reaction system by the ordinary work-up procedures (extraction with an organic solvent, necessary, further purification is carried out by silica gel column chromatography or crystallization.

The starting materials of the present invention described above, 2'-O,3'-N-bis(benzyloxycarbonyl)-N-demethylerythromycin A and B can be prepared according to the method described in Japanese Patent Application Laid-Open No. 27998/86 and Japanese Patent Application Laid-Open No. 92692/83. Furthermore, 6-O-methylerythromycin A and B are disclosed in U.S. Pat. No. 4,331,803 and European Pat. No. 80,818, and the 2'-O-acyl derivatives of 6-O- and 6,11-di-O-erythromycin A and B are disclosed in Japanese Patent Application Laid-Open No. 200998/86.

The compounds of the present invention have strong in vitro and in vivo antibacterial activities against Gram-positive bacteria including erythromycin resistant bacteria and Gram-negative bacteria, therefore, they are useful as antibacterial agents. For the purpose, these compounds may be administered orally or parenterally in a conventional dosage form such as tablet, capsule, powder, troche, ointment, suspension or solution prepared according to conventional pharmaceutical practices.

The compound of formula I can be administered at a dosage of from about 1 mg/kg to 50 mg/kg of body weight per day.

The $LD_{50}$ value of the compound of formula I in mice is in excess of 5000 mg/kg of body weight.

EXPERIMENT 1

In vitro antibacterial activity:

The antibacterial activity of the compounds of formula I against various bacteria was measured using sensitive disc media (produced by Eiken Chemical Co.) according to the MIC method specified by the Japan Chemotherapeutic Society. Erythromycin A, 4''-deoxy-erythromycin A and 6-O-methylerthromycin A were used as the comparative drugs.

The results, indicated as MIC value (minimum inhibitory concentration, mcg/ml), are shown in Table 1.

TABLE 1

| Test micro-organism | In vitro Antibacterial activity | | | | |
|---|---|---|---|---|---|
| | A | B | C | D | E |
| Bacillus cereus ATCC 9634 | 0.2 | 0.1 | 0.1 | 0.1 | 0.1 |
| Bacillus subtilis ATCC 6633 | 0.1 | 0.2 | 0.1 | 0.05 | 0.1 |
| Staphylococcus | 0.2 | 0.39 | 0.1 | 0.1 | 0.39 |

TABLE 1-continued

| Test micro-organism | In vitro Antibacterial activity | | | | |
|---|---|---|---|---|---|
| | A | B | C | D | E |
| aureus Smith 4 | | | | | |
| Staphylococcus aureus J-70 | >100 | 12.5 | >100 | 3.13 | 12.5 |
| Staphylococcus aureus J-105 | >100 | 100 | >100 | 50 | 50 |
| Staphylococcus faecalis ATCC 8043 | 0.05 | 0.05 | 0.025 | 0.025 | 0.05 |
| Escherichia coli K-12 | 12.5 | 0.78 | 3.13 | 0.78 | 0.39 |
| Micrococcus luteus NIHJ | ≦0.025 | 0.025 | ≦0.025 | ≦0.025 | 0.05 |

(Note)
A: erythromycin A
B: 4"-deoxyerythromycin A
C: 6-O—methylerythromycin A
D: 4"-deoxy-6-O—methylerythromycin A (Compound 11)
E: 2'-O—acetyl-4"-deoxy-6-O—methylerythromycin A (Compound 20)

Subsequently, the present invention will be illustrated in more detail by the following Examples.

EXAMPLE 1

Preparation of 4"-deoxy-6-O-methylerythromycin B (Compound 4)

(1) To a solution of 2'-O,3'-N-bis(benzyloxycarbonyl)-N-demethylerythromycin B (10 g, 10.29 mmole) in 100 ml of 1,2-dichloroethane was added 1,1'-thiocarbonyldiimidazole (5.5 g, 30.86 mmole), and the mixture was stirred at 50° C. for 20 hours. The reaction solution was poured into water, adjusted to pH 10 with aqueous ammonia and extracted with dichloromethane. The organic layer was washed with a saturated aqueous sodium chloride solution and dried over anhydrous magnesium sulfate, and the solvent was evaporated. The resulting crude product was purified by silica gel chromatography with dichloromethane as an eluent to give 9.57 g of 4"-O-(1-imidazolyl)thiocarbonyl-2'-O,3'-N-bis(benzyloxycarbonyl)-N-demethylerythromycin B (Compound 1) as a pale yellow powder.

m.p. 185–188° C. (recrystallized from dichloromethane-diethyl ether)

TLC: Rf=0.69 (eluent; dichloromethane:ethyl acetate=2:1)

Elementary analysis for $C_{56}H_{79}N_3O_{16}S$: Calcd. (%) C62.15, H 7.36, N 3.88; Found (%) C 62.27, H 7.57, N 3.61.

(2) To a solution of Compound 1 (4.33 g, 4 mmole) and methyl iodide (1.2 ml, 20 mmole) in 100 ml of DMSO-DME (1:1) was added under ice-cooling 85% potassium hydroxide powder (395 mg, 6 mmole), and the mixture was stirred first at 0°–5° C. for 1.5 hours, then at room temperature for 1.5 hours. To the reaction solution was added 6 ml of triethylamine, and the mixture was stirred at room temperature for 30 minutes and then diluted with 300 ml of ethyl acetate. The ethyl acetate layer was washed with 200 ml of a saturated aqueous sodium chloride solution and dried over anhydrous magnesium sulfate, and the solvent was evaporated. 5.1 g of the resulting crude product was purified by silica gel column chromatography (20 cm×3.5 cm, eluent; dichloromethane) to give 3.35 g of 4"-O-(1-imidazolyl)thiocarbonyl-6-O-methyl-2'-O,3'-N-bis(benzyloxycarbonyl)-N-demethylerythromycin B (Compound 2) as a white foam.

m.p. 101°–103° C. (recrystallized from dichloromethane-petroleum ether)

(3) To a solution of Compound 2 (1.6 g, 1.46 mmole) in 20 ml of benzene were added 97% tributyltin hydride (2 ml, 7.21 mmole) and α,α'-azobis(isobutyronitrile) (100 ml, 0.61 mmole), and the mixture was stirred at 60° C. for 4.5 hours. The reaction solution was diluted with 100 ml of benzene and poured into 100 ml of dil. aqueous ammonia. The organic layer was washed with a saturated aqueous sodium chloride solution and dried over anhydrous magnesium sulfate, and the solvent was evaporated. The resulting crude product was purified by silica gel column chromatography (12 cm×3.5 cm, eluent; dichloromethane) to give 890 mg of 4"-deoxy-6-O-methyl-2'-O,3'-N-bis(benzyloxycarbonyl)-N-demethylerythromycin B (Compound 3) as a white foam.

(4) A mixture of Compound 3 (125 mg, 0.13 mmole), 100 mg of 10% palladium-carbon and 100 mg of ammonium formate in methanol was refluxed for 8 hours. Thereafter, 0.1 ml of 35% aqueous formaldehyde and 0.2 ml of formic acid were added, and the mixture was refluxed for a further 3 hours. The methanol was evaporated under reduced pressure, water was added, and the mixture was adjusted to pH 10 with a saturated aqueous sodium carbonate solution and extracted with dichloromethane. The dichloromethane layer was washed with a saturated aqueous sodium chloride solution and dried over anhydrous magnesium sulfate, and evaporation of the solvent gave 60 mg of 4"-deoxy-6-O-methylerythromycin B (Compound 4).

m.p. 197–198° C. (recrystallized from dichloromethane-diethyl ether)

TLC: Rf=0.65 (eluent; chloroform:methanol=4:1)

IR$\nu_{max}^{KBr}$ cm$^{-1}$: 3400–3480, 1725, 1690

Mass (SIMS): m/e=716 (MH+)

$^1$H-NMR (200 MHz, CDCl$_3$) δ=2.28 [6H, N(CH$_3$)$_2$], 3.12 (3H, 6-OCH$_3$), 3.27 (3H, 3"-OCH$_3$)

$^{13}$C-NMR (50.3 MHz, CDCl$_3$) δ=219.6 (C-9, C=O), 176.0 (lactone C=O), 78.7 (C-6), 70.5 (C-3"), 61.6 (C-5"), 50.9 (6-OCH$_3$), 49.3 (3"-OCH$_3$), 45.5 (C-4"), 25.5 and 22.1 (3"-CH$_3$ and 5"-CH$_3$), 19.9 (6-CH$_3$)

EXAMPLE 2

Preparation of 4"-deoxy-6-O-methylerythromycin B (Compound 4)—Alternative method (1) To a solution of 2'-O-benzyloxycarbonylerythromycin B (4 g, 4.71 mmole) in 50 ml of 1,2-dichloroethane was added 1,1'-thiocarbonyldiimidazole (2 g, 11.24 mmole), and the mixture was stirred at room temperature for 4 days. After the treatment according to the procedure similar to that of Example 1 (1), purification by silica gel column chromatography with chloroform-acetone (4:1) as an eluent gave 3.62 g of 2'-O-benzyloxycarbonyl-4"-O-(1-imidazolyl)thiocarbonylerythromycin B (Compound 5) as a white foam.

TLC: Rf=0.63 (eluent; chloroform:acetone=1:1)

$^1$H-NMR (200 MHz, CDCl$_3$) δ=2.29 [6H, N(CH$_3$)$_2$], 3.37 (3H, 3"-OCH$_3$), 5.21 (2H, benzyl), 7.40 (5H, benzyl), 7.07, 7.62, 8.31 (3H, imidazolyl)

Elementary Analysis for $C_{49}H_{75}N_3O_{14}S$:

Calcd. (%): C61.17, H 7.86, N 4.37;

Found (%): C60.83, H 7.62, N 4.48

(2) To a solution of Compound 5 (3.62 g, 3.77 mmole) in DMSO-DME (20 ml—20 ml) was added under ice-cooling methyl iodide (1.17 ml, 18.85 mmole). Thereafter, 60% sodium hydrate (272 mg, 6.79 mmole) was added, and the mixture was stirred at 0°–5° C. for 1.5 hours.

After the treatment according to the procedure similar to that of Example 1 (2), purification by silica gel column chromatography with chloroform-acetone (4:1) as an eluent gave 1.54 g of 2'-O-benzyloxycarbonyl-4''-O-(1-imidazolyl)thiocarbonyl-6-O-methylerythromycin B (Compound 6) as a white foam.

$^1$H-NMR (200 MHz, CDCl$_3$) δ=2.30 [6H, N(CH$_3$)$_2$], 3.06 (3H, 6-OCH$_3$), 3.38 (3H, 3''-OCH$_3$)

(3) To a solution of Compound 6 (1.4 g, 1.44 mmole) in 10 ml of benzene were added 97% tributyltin hydride (1.4 ml, 5.05 mmole) and α,α'-azobis(isobutyroylnitrile) (20 mg, 0.12 mmole), and the mixture was stirred at 50° C. for 6 hours.

After the treatment according to the procedure similar to that of Example 1 (3), purification by silica gel column chromatography with benzene-acetone (4:1) as an eluent gave 260 mg of 2'-O-benzyloxycarbonyl-4''-deoxy-6-O-methylerythromycin B (Compound 7).

m.p. 135°–140° C. (recrystallized from dichloromethane-petroleum ether)

$^1$H-NMR (200 MHz, CDCl$_3$) δ=2.28 [6H, N(CH$_3$)$_2$], 3.08 (3H, 6-OCH$_3$), 3.27 (3H, 3''-OCH$_3$)

(4) Compound 7 (200 mg, 0.24 mmole) and sodium bicarbonate (100 mg, 1.19 mmole) in a mixture of 5 ml of methanol and 5 ml of water were stirred at 60° C. for 4 hours. The reaction solution was poured into a saturated aqueous sodium carbonate solution and extracted with 100 ml of chloroform. The organic layer was washed with, in turn, a saturated aqueous sodium chloride solution and water, and dried over anhydrous magnesium sulfate. The solvent was evaporated and 170 mg of the residue was purified by silica gel column chromatography with chloroform-methanol (97:3) as an eluent to give 83 mg of 4''-deoxy-6-methylerythromyein B (Compound 4), which was identical with the compound obtained in Example 1 (4) by the mixed melting point test.

EXAMPLE 3

Preparation of 4''-deoxy-6-O-methylerythromycin A (Compound 11)

(1) A solution of 2'-O,3'-N-bis(benzyloxycarbonyl)-N-demethylerythromycin A (10 g, 0.01 mole) in 100 ml of 1,2-dichloroethane was added 1,1'-thiocarbonyldiimidazole (7 g, 0.39 mole), and the mixture was stirred at 60° C. for 10 hours. After the treatment according to the procedure similar to that of Example 1 (1), the resulting crude product was purified by silica gel column chromatography with dichloromethane-ethyl acetate (4:1) as an eluent to give 9.3 g of 4''-O-(1-imidazolyl)thiocarbonyl-2'-O,3'-N-bis(benzyloxycarbonyl)-N-demethylerythromycin A (Compound 8) as a yellow foam.

m.p. 179°–181° C. (recrystallized from ethyl acetate)

Elementary analysis for C$_{56}$H$_{79}$N$_3$O$_{17}$S: Calcd. (%) C 61.24, H 7.25, N 3.83; Found (%) C 61.64, H 7.41, N 3.66.

(2) To a solution of Compound 8 (3.3 g, 3 mmole) and methyl iodide (0.93 ml, 15 mmole) in 40 ml of dimethyl sulfoxide-tetrahydrofuran (1:1) was added under ice-cooling 85% potassium hydroxide powder (237 mg, 3.6 mmole), and the mixture was stirred first at 0°–5° C. for one hour, then at room temperature for 3 hours.

After the treatment according to the procedure similar to that of Example 1 (2), the resulting crude product was purified by silica gel column chromatography with dichloromethane-ethyl acetate (4:1) as an eluent to give 970 mg of 4''-O-(1-imidazolyl)thiocarbonyl-6-O-methyl-2'-O,3'-N-bis(benzyloxycarbonyl)-N-demethylerythromycin A (Compound 9).

m.p. 131°–134° C. (recrystallized from dichloromethane-n-hexane)

(3) To a solution of Compound 9 (1.4 g, 1.26 mmole) in 20 ml of benzene were added tributyltin hydride (2 ml, 7.21 mmole) and α,α'-azobis(isobutyronitrile) (100 mg, 0.61 mmole), and the mixture was stirred at 60° C. under a nitrogen atmosphere for 3 hours.

The treatment according to the procedure similar to that of Example 1 (3) gave 1.04 g of 4''-deoxy-6-O-methyl-2'-O,3'-N-bis(benzyloxycarbonyl)-N-demethylerythromycin A (Compound 10) as a white foam.

m.p. 104°–107° C. (recrystallized from ethyl acetate-n-hexane)

(4) A mixture of Compound 10 (510 mg, 0.517 mmole), 70 mg of 10% palladium-carbon, 300 mg of sodium acetate, 0.1 ml of acetic acid, 2 ml of water and 20 ml of methanol was stirred at room temperature under a hydrogen atmosphere for an hour. 2 ml of 35% aqueous formaldehyde solution was added, the mixture was stirred for a further 3 hours, and the catalyst was removed by filtration. The methanol was evaporated under reduced pressure, the residue was adjusted to pH 10 with a saturated aqueous sodium carbonate solution, and extracted with 100 ml of dichloromethane. The dichloromethane layer was washed, in turn, with a saturated aqueous sodium chloride solution and water, and dried over anhydrous magnesium sulfate. The solvent was evaporated, and 380 mg of the resulting residue was purified by silica gel column chromatography (30 cm×1.8 cm, eluent; methanol:chloroform=3:97) to give 126 mg of 4''-deoxy-6-O-methylerythromycin A (Compound 11) as a white foam.

m.p. 148°–151° C. (recrystallized from ethanol)

IR$\nu_{max}^{KBr}$cm$^{-1}$: 3440, 1727, 1685

Mass (FD): m/e=731 (M$^+$)

$^1$H-NMR (200 MHz, CDCl$_3$) δ=2.28 [6H, N(CH$_3$)$_2$], 3.06 (3H, 6-OCH$_3$), 3.26 (3H, 3''-OCH$_3$)

$^{13}$C-NMR (50,3 MHz, CDCl$_3$) δ=221.0 (C-9, C=O), 175.8 (lactone, C=O), 78.3 (C-6), 70.5 (C-3''), 61.5 (C-5''), 50.7 (6-OCH$_3$), 49.3 (3''-OCH$_3$), 45.6 (C-4''), 40.3 [N(CH$_3$)$_2$], 25.5 and 22.1 (3''-CH$_3$ and 5''-CH$_3$), 19.7 (6-CH$_3$)

Elementary Analysis for C$_{38}$H$_{69}$NO$_{12}$: Calcd. (%): C62.35, H 9.50, N 1.91; Found (%): C62.33, H 9.62, N 1.76

EXAMPLE 4

Preparation of 4''-deoxy-6,11-di-O-methylerythromycin A (Compound 14)

(1) (Method A) To a solution of Compound 8 (3 g, 2.73 mmole), obtained in Example 3 (1), in a mixture of DMSO (15 ml) and DME (15 ml) were added under ice-cooling methyl iodide (0.93 ml, 13.66 mmole), and the mixture was stirred for 2 hours. To a reaction solution was added 6 ml of triethylamine, and the mixture was diluted with 200 ml of ethyl acetate. The ethyl acetate layer was washed with 100 ml of a saturated aqueous sodium chloride solution and dried over anhydrous magnesium sulfate. The solvent was evaporated, and the resulting residue was purified by silica gel column chromatography (inside size 26 cm×3.5 cm, eluent; dichloromethane:ethyl acetate=4:1) to give 1.58 g of 4''-O-(1-imidazolyl)thiocarbonyl-6,11-di-O,3''-N- bis(benzyloxycarbonyl)-N-demethylerythromycin A (Compound 12) as a white foam.

m.p. 201°–203° C. (recrystallized from ethyl acetate-n-hexane)

Elementary Analysis for $C_{58}H_{83}N_3O_{17}S$: Calcd. (%): C 61.85, H 7.43, N 3.73; Found (%): C 62.17, H 7.29, N 3.64.

(1) (Method B) To a solution of 2'-O,3'-N-bis(benzyloxycarbonyl)-N-demethylerythromycin A (9.88 g, 10 mmole) and 5 ml of methyl iodide in 100 ml of DMSO-DME (1:1) was added at once under ice-cooling with stirring 1.32 g of 85% potassium hydroxide, and then the mixture was stirred for 2 hours. To the reaction solution was added 7.5 ml of 50% aqueous dimethylamine solution and the mixture was stirred for 30 minutes. The reaction solution was poured into 500 ml of water with stirring, and the solid which formed was collected by filtration, washed with water and dried. The solution of 9.8 g of the resulting solid in 10 ml of dichloromethane was passed through silica gel column (30 g) eluting with dichloromethane. The combined eluting solution was concentrated under reduced pressure to give 4.5 g of a white foam. A solution of the foam in diethyl ether was concentrated twice under reduced pressure, and crystallized from diethyl ether-petroleum ether to give 3.6 g of 6, 11-di-O-methyl-2'-O,3'-N-bis(benzyloxycarbonyl)-N-demethylerythromycin A.

IR$\nu_{max}^{KBr}$ cm$^{-1}$ d 3380, 1730, 1700

$^1$H-NMR (200 MHz, CDCl$_3$) $\delta$ = 3.07 (6-OCH$_3$), 3.57 (11-OCH$_3$)

$^{13}$C-NMR (50.3 MHz, CDCl$_3$) $\delta$ = 50.4 (6-OCH$_3$), 60.9 (11-OCH$_3$)

To a solution of 6,11-di-O-methyl-2'-O-3'-N-bis(benzyloxycarbonyl)-N-demethylerythromycin A (2 g, 1.97 mmole), obtained in the above, in 20 ml of 1,2-dichloroethane was added 1,1'-thiocarbonyldiimidazole (1.5 g, 8.42 mmole), and the mixture was stirred at 50° C. for 5 hours and refluxed for 14 hours. The reaction solution was poured into water, adjusted to pH 10 with aqueous ammonia and extracted with dichloromethane. The organic layer was washed with a saturated aqueous sodium chloride solution and dried over anhydrous magnesium sulfate, and the solvent was evaporated under reduced pressure. The residue was purified by silica gel column chromatography (18 cm×3.5 cm, eluent; benzene:acetone=5:1) to give 1.95 g of 4''-O-(1-imidazolyl)thiocarbonyl-6,11-di-O-methyl-2'-O,3'-N-bis(benzyloxycarbonyl)-N-demethylerythromycin A (Compound 12) as a white foam, which was identical with that obtained in the above method A.

(2) To a solution of Compound 12 (1.19 g, 1.69 mmole), obtained in the method A or B, in 20 ml of benzene were added 97% tributyltin hydride (1.5 ml, 5.41 mmole) and α,α'-azobis(isobutyronitrile) (19 mg, 0.12 mmole), and the mixture was stirred at 50° C. for 6 hours.

After the treatment according to the procedure similar to that of Example 1 (3), the resulting crude product was purified by silica gel column chromatography with benzene-acetone (10:1) as an eluent to give 820 mg of 4''-deoxy-6,11-di-O-methyl-2'-O,3'-N-bis(benzyloxycarbonyl)-N-demethylerythromycin A (Compound 13).

TLC: Rf=0.66 (eluent; benzene:acetone=4:1)

(3) A mixture of Compound 13 (360 mg, 0.36 mmole), 10% palladium-carbon (360 mg) and ammonium formate (280 mg, 4.44 mmole) in methanol (20 ml) was refluxed for 12 hours. Subsequently, 0.3 ml of 35% formaldehyde and 0.6 ml of formic acid were added, and the mixture was refluxed for a further 5 hours. After treatment according to the procedure similar to that of Example 2 (4), the resulting crude product was purified by silica gel column chromatography with chloroform-methanol (95:5) as an eluent to give 37 mg of 4''-deoxy-6,11-di-O-methylerythromycin A (Compound 14) as a colorless foam.

m.p. 199°–202° C. (recrystallized from dichloromethane-diethyl ether)

TLC: Rf=0.67 (eluent; chloroform:methanol=4:1)

IR$\nu_{max}^{KBr}$ cm$^{-1}$: 3420, 1725, 1710

Mass (SIMS): m/e=746 (MH$^+$)

$^1$H-NMR (200 MHz, CDCl$_3$) $\delta$ = 2.29 [LH, N(CH$_3$)$_2$], 312 (3H, 6OCH$_3$), 3.26 (3H, 3''-OCH$_3$), 3.59 (3H, 11-OCH$_3$)

$^{13}$C-NMR (100.4 MHz, CDCl$_3$) $\delta$ = 217.4 (C-9, C=0), 175.7 (lactone C=0) 79.0 (C-6), 70.5 (C-3''), 61.7 (C-5''), 60.9 (11-OCH$_3$), 50.6 (6-OCH$_3$), 49.3 (3''-OCH$_3$), 45.6 (C-4''), 40.3 [N(CH$_3$)$_2$], 25.6 and 22.2 (3''-CH$_3$ and 5''-CH$_3$), 20.3 (6-CH$_3$)

Elementary Analysis for $C_{39}H_{71}NO_{12}$: Calcd. (%): C 62.79, H 9.59, N 1.88; Found (%): C 62.39, H 9.41, N 1.84.

EXAMPLE 5

Preparation of 4''-deoxy-2'-O-propionyl-6-O-methylerythromycin A (Compound 16)

(1) To a solution of 2'-O-propionyl-6-O-methylerythromycin A (5.4 g, 6.72 mmole) in 50 ml of 1,2-dichloroethane was added 1,1'-thiocarbonyldiimidazole (2.7 g, 15.15 mmole), and the mixture was stirred at room temperature for 5 days.

After the treatment according to the procedure similar to that of Example 1 (1), the resulting crude product was purified by silica gel column chromatography with chloroform-acetone (4:1) as an eluent to give 3.1 g of 4''-O-(1-imidazolyl)thiocarbonyl-2'-O-propionyl-6-O-methylerythromycin A (Compound 15) as a yellow powder.

$^{13}$C-NMR (50.3 MHz, CDCl$_3$) $\delta$ = 221.1 (C-9 C=0), 184.3 (C=S), 175.5 (lactone C=0), 173.3 (propionyl C=0), 136.7, 131.0, 117.9 (imidazolyl), 86.8 (C-4''), 78.3 (C-6), 63.9 and 63.7 (C-5''and C-3'), 50.4 (6-OCH$_3$), 49.5 (3''-OCH$_3$), 40.7 [N(CH$_3$)$_2$], 28.0 (propionyl —CH$_2$—), 19.9 (6-CH$_3$), 9.1 (propionyl —CH$_3$)

(2) To a solution of Compound 15 (3 g, 3.28 mmole) in 40 ml of benzene were added 97% tributyltin hydride (3 ml, 10.8 mmole) and α, α'-azobis(isobutyronitrile) (300 mg, 1.83 mmole), and the mixture was stirred at 60° C. for 9 hours.

After the treatment according to the procedure similar to that of Example 1 (3), the resulting crude product was purified by silica gel column chromatography with benzene-acetone (4:1) as an eluent to give 1.1 g of 4''-deoxy-2'-O-propionyl-6-O-methylerythromycin A (Compound 16).

m.p. 216°–218° C. (recrystallized from ethyl acetate)

$^1$H-NMR (200 MHz, CDCl$_3$) $\delta$ = 2.25 [6H, N(CH$_3$)$_2$], 3.04 (3H, 6-OCH$_3$), 3.30 (3H, 3''-OCH$_3$)

$^{13}$C-NMR (50.3 MHz, CDCl$_3$) $\delta$ = 221.1 (C-9, C=0), 175.6 (lactone C=0) 173.3 (propionyl C=0), 78.3 (C-6), 70.6 (C-3''), 61.6 (C-5''), 50.5 (6-OCH$_3$), 49.2 (3''-OCH$_3$), 45.3 (C-4''), 40.8 [N(CH$_3$)$_2$], 28.1 (propionyl —CH$_2$—), 25.5 and 22.0 (3''-CH$_3$ and 5''-CH$_3$), 19.8 (6-CH$_3$), 9.1 (propionyl —CH$_3$)

Elementary Analysis for $C_{41}H_{73}NO_{13}$: Calcd. (%): C 62.49, H 9.34, N 1.78; Found (%): C 62.31, H 8.88, N 1.83.

EXAMPLE 6

Preparation of 4''-deoxy-2'-O-ethylsuccinyl-6-O-methylerythromycin A(Compound 18)

To a solution of 5 g of 6-O-methylerythromycin A in 50 ml of dichloromethane were added 2.8 g of sodium bicarbonate and 1.32 g of ethylsuccinyl chloride, respectively, and the mixture was stirred at room temperature for 5 hours. The reaction solution was poured into water, and the dichloromethane layer was collected, washed with water and dried. The solvent was evaporated and 6.6 g of the resulting crude 2'-O-ethylsuccinyl -6-O-methyerytromycin A was allowed to react according to the procedure similar to that of Example 5 (1) to give 4''-O-(1-imidazolyl)thiocarbonyl-2'-O-ethylsuccinyl-6-O-methylerythromycin A (Compound 17, m.p. 200°–203° C.). Compound 17 was reacted according to the procedure similar to that of Example 5 (2) to give 1.94 g of the title compound.

m.p. 174°–176° C. (recrystallized from diethyl ether-petroleum ether)

$^1$H-NMR (200 MHz, CDCl$_3$). δ=2.24 [6H, N(CH$_3$)$_2$], 2.64 (4H, —COCH$_2$CH$_2$) 3.04 (3H, 6OCH$_3$), 3.30 (3H, 3''-OCH$_3$), 4.17 (2H, —OCH$_2$CH$_3$)

$^{13}$C-NMR (50.3 MHz, CDCl$_3$) δ=221.1 (C-9 C=O), 175.7 (lactone C=O), 172.2 and 171.1 (ethylsuccinyl C=O), 78.3 (C-6), 70.6 (C-3''), 63.4 (C-3'), 61.6 (C-5''), 60.6 (ethylsuccinyl CH$_2$CH$_3$), 50.5 (6-OCH$_3$), 49.2 (3''OCH$_3$), 45.4 (C-4''), and 29.6 and 29.4 (ethylsuccinyl —COCH$_2$CH$_2$), 25.5 and 22.0 (3''-CH$_3$ and 5''-CH$_3$), 19.8 (6-CH$_3$), 14.3 (ethylsuccinyl —CH$_3$)

EXAMPLE 7

Preparation of 2'-O-acetyl-4''-deoxy-6-O-methylerythromycin A (Compound 20)

2'-O-acetyl-6-O-methylerythromycin A (5 g, 6.3 mmole) was reacted according to the procedure similar to that of Example 5 (1) to give 4.27 g of 4''-O-(1-imidazolyl)thiocarbonyl-2'-O-acetyl-6-O-methylerythromycin A (Compound 19, m.p. 200°–205° C.). Compound 19 was reacted according to the procedure similar to that of Example 5 (2) to give 1.93 g of the title compound.

m.p. 230°–232° C. (recrystallized from dichloromethanen-hexane)

IR $v_{max}^{KBr}$ cm$^{-1}$: 3450, 1780, 1760, 1685

$^1$H-NMR (200 MHz, CDCl$_3$) δ=0.84 (3H, 14-CH$_3$), 2.04 (3H, —COCH$_3$), 2.26 [6H, N(CH$_3$)$_2$], 3.03 (3H, 6-OCH$_3$), 3.29 (3H, 3''-OCH$_3$), $^{13}$C-NMR (50.3 MHz, CDCl$_3$) δ=221.1 (C-9 C=O), 175.6 (lactone C=O), 170.0 (acetyl C=O), 78.3 (C-6), 70.6 (C-3''), 61.7 (C-5''), 50.5 (6-OCH$_3$), 49.2 (3''-OCH$_3$), 45.3 (C-4''), 40.7 [N(CH$_3$)$_2$], 25.5 and 22.0 (3''-CH$_3$ and 5''-CH$_3$), 21.3 (acetyl —CH$_3$), 19.8 (6-CH$_3$)

EXAMPLE 8

Preparation of 4''-deoxy-6-O-methylerythromycin A (Compound 11)

Compound 20 (1.3 g, 7 mmole) obtained in Example 7 and sodium bicarbonate (0.5 g, 6 mmole) in a mixture of 50 ml of methanol and 20 ml of water were stirred at room temperature for 20 hours. Most of the methanol was evaporated under reduced pressure, and the mixture was extracted with dichloromethane. The organic layer was washed with a saturated aqueous sodium chloride solution and water, respectively, and dried over anhydrous magnesium sulfate. The solvent was evaporated and the residue was purified by silica gel column chromatography with chloroform-methanol (97:3) as an eluent to give 1 g of the title compound, which was identical with the compound obtained in Example 3 by the mixed melting point test.

EXAMPLE 9

Preparation of 4''-deoxy-2'-O-ethylsuccinyl-6-O-methylerythromycin A (Compound 18)

To a solution of Compound 11 (280 mg, 0.38 mmole) in 10 ml of dichloromethane was added sodium bicarbonate (200 mg, 2.38 mmole) followed by ethylsuccinyl chloride (90 mg, 0.54 mmole), and the mixture was stirred at room temperature for 6 hours. The reaction solution was poured into water and extracted with dichloromethane, and the extract was washed with a saturated aqueous sodium bicarbonate solution and water, respectively, and dried over anhydrous magnesium sulfate. The solvent was evaporated and the residue was purified by silica gel colum chromatography with chloroformacetone (4:1) as an eluent to give 120 mg of the title compound.

m.p. 175°–178° C. (recrystallized from diethyl ether-n-hexane)

What is claimed is:

1. Erythromycin derivatives represented by the general formula

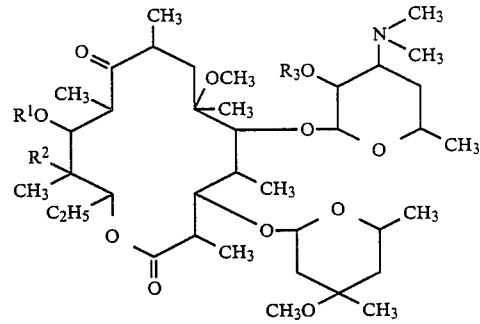

wherein $R^1$ is a hydrogen atom or a methyl group, $R^2$ is a hydrogen atom or a hydroxy group, $R^3$ is a hydrogen atom, a lower alkanoyl group, an alkoxycarbonyl group or an alkylsuccinyl group, and the salts thereof.

2. 4''-deoxy-6-O-methlerythromycin A.
3. 2'-O-acetyl-4''-deoxy-6-O-methylerythromycin A.
4. 2'-O-propionyl-4''-deoxy-6-O-methylerythromycin A.
5. 2'-O-ethylsuccinyl-4''-deoxy-6-O-methylerythromycin A.

* * * * *

UNITED STATES PATENT AND TRADEMARK OFFICE
CERTIFICATE OF CORRECTION

PATENT NO. : 4,833,236

DATED : May 23, 1989

INVENTOR(S) : MORIMOTO et al

It is certified that error appears in the above-identified patent and that said Letters Patent is hereby corrected as shown below:

Col. 2, line 47, "ocarbonyloxyl" should read --ocarbonyloxy--;

line 65, "4''-deoxy-6-O-methyl-3''" should read --4''-deoxy-6-O-methyl-3'--.

Col. 4, line 20, after "vent," insert --washing with water, dryness, and concentration). If--.

Col. 7, line 56, "C 61.64" should read --C 61.61--.

Col. 8, line 58, after "mmole)" insert --and 85% potassium hyroxide (477 mg, 6.55 mmole),--;

line 68, "4''-O-(1-imidazolyl)thiocarbonyl-6,11-di-O,3''-N-" should read --4''-O-(1-imidazolyl)thiocarbonyl-6,11-di-O-methyl-2'-O,3'-N- --.

UNITED STATES PATENT AND TRADEMARK OFFICE
CERTIFICATE OF CORRECTION

PATENT NO. : 4,833,236

DATED : May 23, 1989

INVENTOR(S) : MORIMOTO et al

It is certified that error appears in the above-identified patent and that said Letters Patent is hereby corrected as shown below:

Col. 10, line 14, "LH" should read --6H--;

line 15, "312" should read --3.12-- and "6OCH$_3$" should read --6-OCH$_3$--.

Col. 11, line 20, "-6-O-methyerytromycin" should read -- -6-O-methylerythromycin--;

line 31, "6OCH$_3$" should read --6-OCH$_3$--;

line 37, "3''OCH$_3$" should read --3''-OCH$_3$--;

line 57, "thanen-hexane" should read --thane-n-hexane--.

UNITED STATES PATENT AND TRADEMARK OFFICE
CERTIFICATE OF CORRECTION

PATENT NO. : 4,833,236

DATED : May 23, 1989

INVENTOR(S) : MORIMOTO et al

It is certified that error appears in the above-identified patent and that said Letters Patent is hereby corrected as shown below:

Col. 12, line 35, "colum" should read --column--;

line 36, "roformacetone" should read --roform-acetone--

Signed and Sealed this

Seventeenth Day of April, 1990

Attest:

HARRY F. MANBECK, JR.

Attesting Officer

Commissioner of Patents and Trademarks